(12) United States Patent
Hansen et al.

(10) Patent No.: US 10,119,154 B2
(45) Date of Patent: Nov. 6, 2018

(54) ANTHOCYANINS WITH SPECIFIC PROPERTIES

(71) Applicant: Evolva SA, Reinach (CH)

(72) Inventors: Jorgen Hansen, Frederiksberg (DK); Patricia Hoyle, Basel (CH); Michael Naesby, Basel (CH); Joseph M. Sheridan, Hertfordshire (GB); Jonathan R. Heal, Nottingham (GB)

(73) Assignee: Evolva SA, Reinach (CH)

(*) Notice: Subject to any disclaimer, the term of this patent is extended or adjusted under 35 U.S.C. 154(b) by 564 days.

(21) Appl. No.: 14/654,291

(22) PCT Filed: Dec. 23, 2013

(86) PCT No.: PCT/EP2013/077943
§ 371 (c)(1),
(2) Date: Oct. 26, 2015

(87) PCT Pub. No.: WO2014/096456
PCT Pub. Date: Jun. 26, 2014

(65) Prior Publication Data
US 2015/0344920 A1    Dec. 3, 2015

Related U.S. Application Data

(60) Provisional application No. 61/740,828, filed on Dec. 21, 2012.

(51) Int. Cl.
| | |
|---|---|
| C12P 17/06 | (2006.01) |
| C12N 15/52 | (2006.01) |
| C12N 15/10 | (2006.01) |
| C12P 19/44 | (2006.01) |
| C12N 9/10 | (2006.01) |

(52) U.S. Cl.
CPC ............ C12P 17/06 (2013.01); C12N 9/1025 (2013.01); C12N 9/1048 (2013.01); C12N 15/1079 (2013.01); C12N 15/52 (2013.01); C12P 19/44 (2013.01); C12Y 203/00 (2013.01); C12Y 204/00 (2013.01)

(58) Field of Classification Search
CPC .......................... C12N 9/1025; C12N 9/1048; C12N 15/1079; C12N 15/52; C12P 19/44; C12P 17/06; C12Y 203/00; C12Y 204/00
See application file for complete search history.

(56) References Cited

FOREIGN PATENT DOCUMENTS

| EP | 1811030 A1 | 7/2007 |
|---|---|---|
| WO | 2009009906 A1 | 1/2009 |
| WO | 2010114568 A1 | 10/2010 |

OTHER PUBLICATIONS

Venkiteswaran (Master's Thesis, 2011, ProQuest Dissertations Publishing).*

(Continued)

*Primary Examiner* — Jeremy C Flinders
(74) *Attorney, Agent, or Firm* — McDonnell Boehnen Hulbert & Berghoff LLP

(57) ABSTRACT

The present disclosure provides methods for identifying anthocyanins with improved stability, color, or hue using a screening method, and producing anthocyanins with improved stability, color, or hue in, for example, host cells comprising one or more heterologous glycosyltransferase nucleic acid molecules and one or more heterologous acyltransferase nucleic acid molecules.

20 Claims, 3 Drawing Sheets

(56) References Cited

OTHER PUBLICATIONS

Yonekura-Sakakibara et al., "Two glycosyltransferases involved in anthocyanin modification delineated by transcriptome independent component analysis in *Arabidopsis thaliana*", The Plant Journal, 69:154-167 (2012).
Rose et al., "Purification and characterization of glycosyltransferases involved in anthocyanin biosynthesis in cell-suspension cultures of *Daucus carota* L.", Planta, 198:397-403 (1996).
Gläβgen et al., "Regulation of enzymes involved in anthocyanin biosynthesis in carrot cell cultures in response to treatment with ultraviolet light and fungal elicitors", Planta, 204:409-498 (1998).
Nishihara et al., "Genetic engineering of flavonoid pigments to modify flower color in floricultrual plants", Biotechnol. Lett., 33:433-441 (2011).
International Search Report dated Mar. 14, 2014, for corresponding PCT application serial No. PCT/EP2013/077943.
Yan et al., "Metabolic Engineering of Anthocyanin Biosynthesis in *Escherichia coil*", Applied and Environmental Microbiology, 71(7):3617-3623 (2005).

\* cited by examiner

ANTHOCYANINS WITH SPECIFIC PROPERTIES

PRIORITY

This application claims the benefit of U.S. Provisional Patent Application Ser. No. 61/740,828 filed on Dec. 21, 2012, which is incorporated herein by reference in its entirety.

FIELD OF THE INVENTION

The present invention relates to the field of anthocyanins and use thereof for various purposes. In particular, the invention relates to methods for producing a large variety of different anthocyanins, and methods for selecting anthocyanins with desired properties. These properties can for example be a specific color, hue or chemical stability of the anthocyanin.

BACKGROUND

Anthocyanins are multi-glycosylated anthocyanidins, which in turn are derived from flavonoids such as naringenin. The anthocyanins are often further acylated in a process where moieties from aromatic or non-aromatic acids are transferred to hydroxyl groups of the anthocyanin-resident sugars. The aromatic acylation of anthocyanins increases stability and shifts their color to blue.

Anthocyanins are pigments, which naturally appear red, purple, or blue. Frequently, the color of anthocyanins is dependent on pH. Anthocyanins are naturally found in flowers, where they provide bright-red and -purple colors. Anthocyanins are also found in vegetables and fruits. Anthocyanins are useful as dyes or coloring agents, and furthermore anthocyanins have caught attention for their antioxidant properties.

Certain anthocyanins are particularly interesting, such as those from strongly colored cultivars of sweet potato, radish and carrot. As purification of these compounds is tedious and expensive, it is commercially desirable to be able to produce the final compounds from precursors.

SUMMARY OF THE INVENTION

The present invention provides methods for identifying anthocyanins with improved color, hue stability or other properties through a screening platform. In particular, the present invention exploits that acylation of glycosylated anthocyanidins stabilizes the molecule against degradation from low pH, high temperatures and also change their color and hue, however, in an unpredictable manner. By creating random combinations of glycosylations and acylations, a multitude of known and novel anthocyanins can be identified by screening for anthocyanins with improved stability or color. Thus, the invention shows that stabilized anthocyanins, or anthocyanins with different color and/or hue can be obtained by altering the acylation and glycosylation pattern anthocyanins with different properties.

Although this invention disclosed herein is not limited to specific advantages or functionality, the invention provides a method of identifying anthocyanins with improved stability, color, or hue using a screening method comprising: (a) providing one or more microbial host cells capable of producing at least one anthocyanidin, wherein said host cells comprise one or more heterologous glycosyltransferase (GT) nucleic acid molecules, one or more heterologous acyltransferase (AT) nucleic acid molecules, or both one or more heterologous GT nucleic acid molecules and one or more heterologous AT nucleic acid molecules; (b) cultivating said host cells under conditions allowing growth of said cells and production of at least one anthocyanin thereby; (c) screening said host cells and/or culture medium for anthocyanins with improved stability, color, or hue; and (d) identifying anthocyanins with improved stability, color, or hue.

In one aspect, the method of identifying anthocyanins with improved stability, color, or hue using a screening method further comprises: (a) isolating one or more anthocyanins from said host cells and/or from culture medium of the host cells; (b) exposing the one or more anthocyanins to steadily increasing concentrations of a reagent to effect a change in the color intensity of the one or more anthocyanins; (c) comparing the concentration where a loss of color intensity occurs with a control, wherein the ability to retain color intensity at higher concentrations of exposure to the reagent than the control indicates improved anthocyanin stability.

In a further aspect, the reagent is a base, light, heat, and/or oxygen. In yet a further aspect, the reagent is a base or a strong base. In another aspect, the reagent comprises lithium hydroxide, sodium hydroxide, potassium hydroxide, and rubidium hydroxide.

In another aspect, the color intensity is determined by spectrophotometry.

In another aspect, the present invention provides a method of identifying a host cell capable of producing an anthocyanin with a predetermined property comprises: (a) providing a composition of microbial host cells, wherein each host cell is capable of producing at least one anthocyanidin, and wherein each host cell comprises one or more heterologous GT nucleic acid molecules, one or more heterologous AT nucleic acid molecules, or both one or more heterologous GT nucleic acid molecules and one or more heterologous AT nucleic acid molecules; (b) cultivating said host cells under conditions allowing growth of said host cells and production of at least one anthocyanin thereby; (c) screening the composition of host cells, for host cells producing an anthocyanin with the predetermined property; and (d) selecting said host cell; wherein a host cell capable of producing an anthocyanin with a predetermined property is identified.

In a further aspect, the predetermined property is improved stability, color or hue.

In another aspect, the present invention provides a method of producing a anthocyanins with improved stability, color, or hue, said method comprising the steps of: (a) providing two or more microbial host cells capable of producing at least one anthocyanidin, wherein each host cell comprises one or more heterologous GT nucleic acid molecules and one or more heterologous AT nucleic acid molecules; (b) cultivating said host cells under conditions allowing growth of said cells and production of anthocyanins thereby; and (c) isolating one or more anthocyanins from the host cells and/or from the culture medium.

The invention discloses one or more host cells are capable of producing an anthocyanidin of the formula I

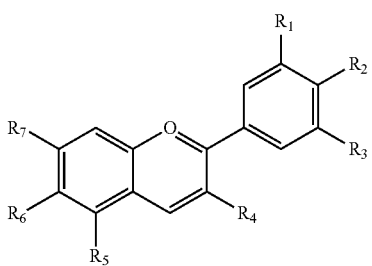

(I)

wherein $R_1$ is selected from the group consisting of —H, —OH and —OCH$_3$; and $R_2$ is selected from the group consisting of —H and —OH; and $R_3$ is selected from the group consisting of —H, —OH and —OCH$_3$; and $R_4$ is selected from the group consisting of —H and —OH; and $R_5$ is selected from the group consisting of —OH and —OCH$_3$; and $R_6$ is selected from the group consisting of —H and —OH; and $R_7$ is selected from the group consisting of —OH and —OCH$_3$ In certain aspects, the anthocyanidin is selected from the group consisting of aurantinidin, cyanidin, delphinidin, europinidin, luteolinidin, pelargonidin, malvidin, peonidin, petunidin and rosinidin.

The invention further discloses one or more host cells comprising one or more heterologous enzyme nucleic acid molecules, and wherein each heterologous enzyme nucleic acid molecule encodes an enzyme of the aurantinidin, cyanidin, delphinidin, europinidin, luteolinidin, pelargonidin, malvidin, peonidin, petunidin or rosinidin biosynthesis pathway. In certain aspects, the host cells are capable of producing cyanidin. In other aspects, the host cells comprise one or more heterologous enzyme nucleic acid molecules each encoding an enzyme of the cyanidin biosynthesis pathway.

In other aspects, the host cell comprises one or more of the following heterologous enzyme nucleic acid molecules encoding the polynucleotides comprising chalcone synthase (CHS), chalcone isomerase (CHI), flavone 3-hydroxylase (F3H), flavonoid 3-hydroxylase (F3'H), flavonoid 3',5'-hydroxylase (F3'5'H), dihydroflavonol 4-reductase (DFR), anthocyanidin synthase (ANS (LDOX)), flavonol synthase (FLS), leucoanthocyanidin reductase (LAR), and anthocyanidin reductase (ANR).

In other aspects, the invention discloses one or more host cells are capable of producing one or more flavanones.

In yet other aspects, one or more host cells comprise one or more heterologous enzyme nucleic acid molecules each encoding an enzyme of the naringenin biosynthesis pathway.

In yet other aspects, one or more host cells comprise one or more of the following heterologous enzyme nucleic acid molecules: (a) a heterologous enzyme nucleic acid molecule encoding naringenin-chalcone synthase; or (b) a heterologous enzyme nucleic acid molecule encoding chalcone isomerase.

In other aspects, the invention provides one or more host cells that are capable of producing a compound selected from the group consisting of coumaroyl-CoA, benzoyl-CoA, sinapoyl-CoA, feruloyl-CoA, malonyl-CoA, cinnamoyl-CoA, and caffeoyl-CoA. In further aspects, the one or more host cells comprise one or more heterologous enzyme nucleic acid molecules each encoding an enzyme of the coumaroyl-CoA biosynthesis pathway.

In yet further aspects, the one or more host cells comprise one or more of the following heterologous enzyme nucleic acid molecules: (a) a heterologous enzyme nucleic acid encoding phenylalanine ammonia lyase (PAL); (b) a heterologous enzyme nucleic acid encoding cinnamate 4-monooxygenase; or (c) a heterologous enzyme nucleic acid encoding 4-coumarate-CoA ligase.

In other aspects, the invention provides at least 10 or more host cells that each comprise different combinations of heterologous GT nucleic acid molecules and/or heterologous AT nucleic acid molecules. In yet other aspects, at least 10 host cells comprise at least 10 different heterologous GT nucleic acid molecules each encoding a different glycosyltransferase.

In further aspects, the glycosyltransferase is a UDP-glucose dependent glucosyltransferase.

In further aspects, the glycosyltransferase is a UDP-glucose dependent glucosyltransferase of family 1.

In yet further aspects, the invention provides at least 10 host cells comprising at least 10 different heterologous AT nucleic acid molecules each encoding a different acyltransferase.

In yet further aspects, the acyltransferase is a BAHD acyltransferase.

In yet a further aspect, each host cell comprises at least one artificial chromosome comprising the heterologous GT nucleic acid molecules and/or heterologous AT nucleic acid molecules.

In yet a further aspect, each host cell comprises at least one artificial chromosome comprising all the heterologous GT nucleic acid molecules and/or heterologous AT nucleic acid molecules comprised within said cell.

The present invention also provides a composition comprising one or more microbial host cells capable of producing one or more anthocyanins, wherein the host cells express at least one anthocyanidin, and wherein the host cells comprise one or more heterologous GT nucleic acid molecules and one or more heterologous AT nucleic acid molecules.

In a certain aspect, the composition comprises two or more host cells, wherein at least two of the host cells comprise different heterologous GT nucleic acid molecules or AT nucleic acid molecules.

In a further aspect, the microbial cell is a yeast cell or a bacterial cell.

DETAILED DESCRIPTION OF THE INVENTION

Screening Platform

Figure 1:
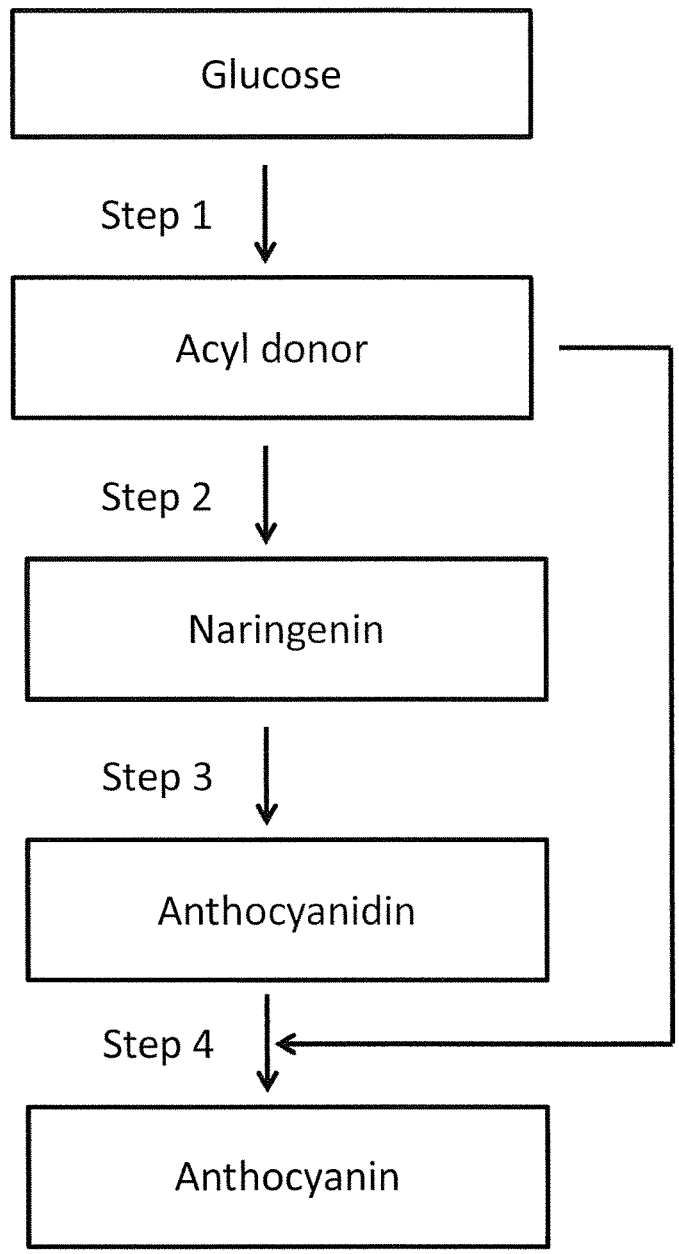
FIG. 1 shows a schematic overview of a pathway to produce anthocyanins according to the invention.
Figure 2:
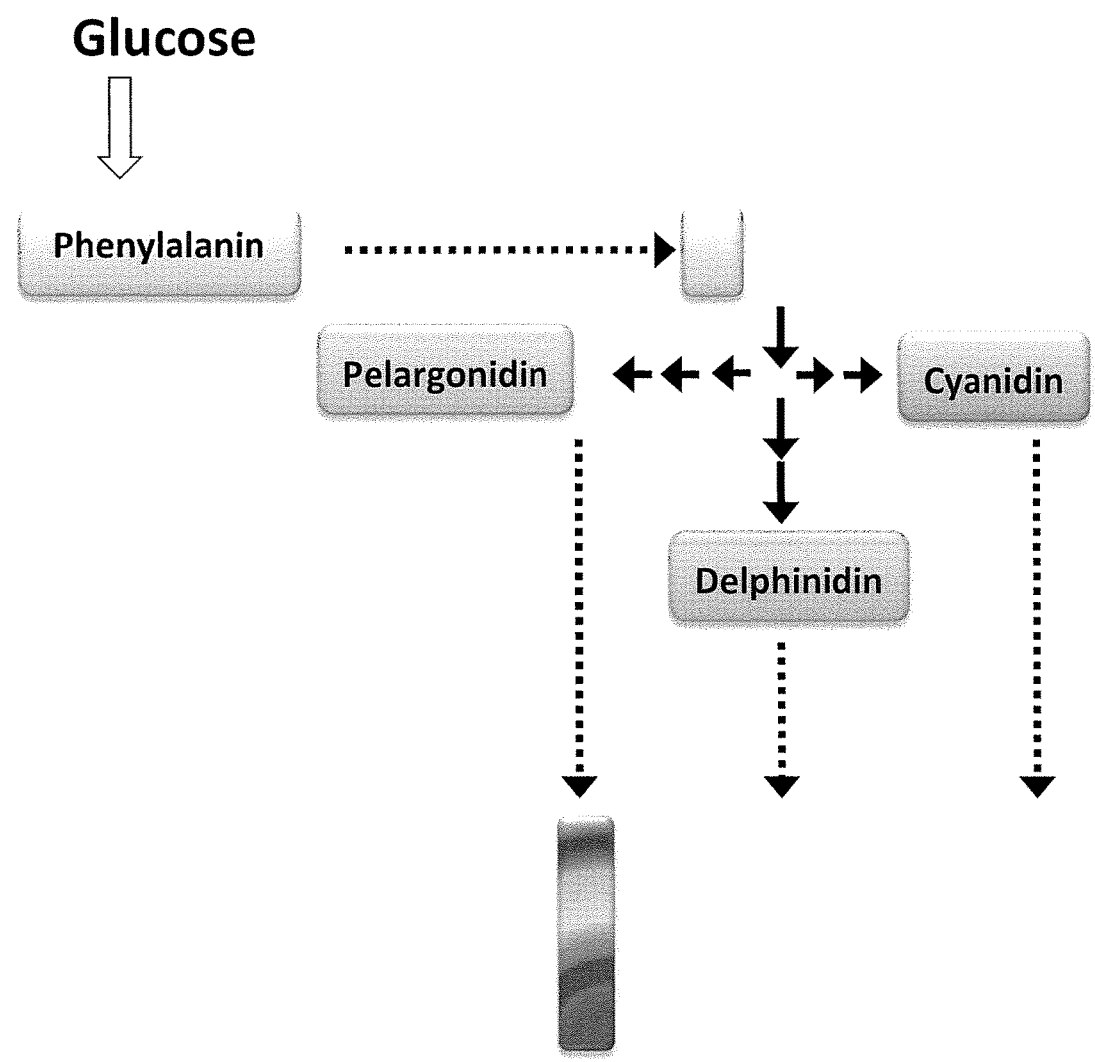
FIG. 2 shows a schematic overview of examples of the pathways to produce anthocyanins according to the invention. In this example a host cell is capable of producing naringenin, and from naringenin the host cells can produce anthocyanidins, e.g. pelargonidin, cyanidin and/or delphinidin. Single or successive different glycosylations and/or acylations form a very large variety of different anthocyanins with different properties.
Figure 3:
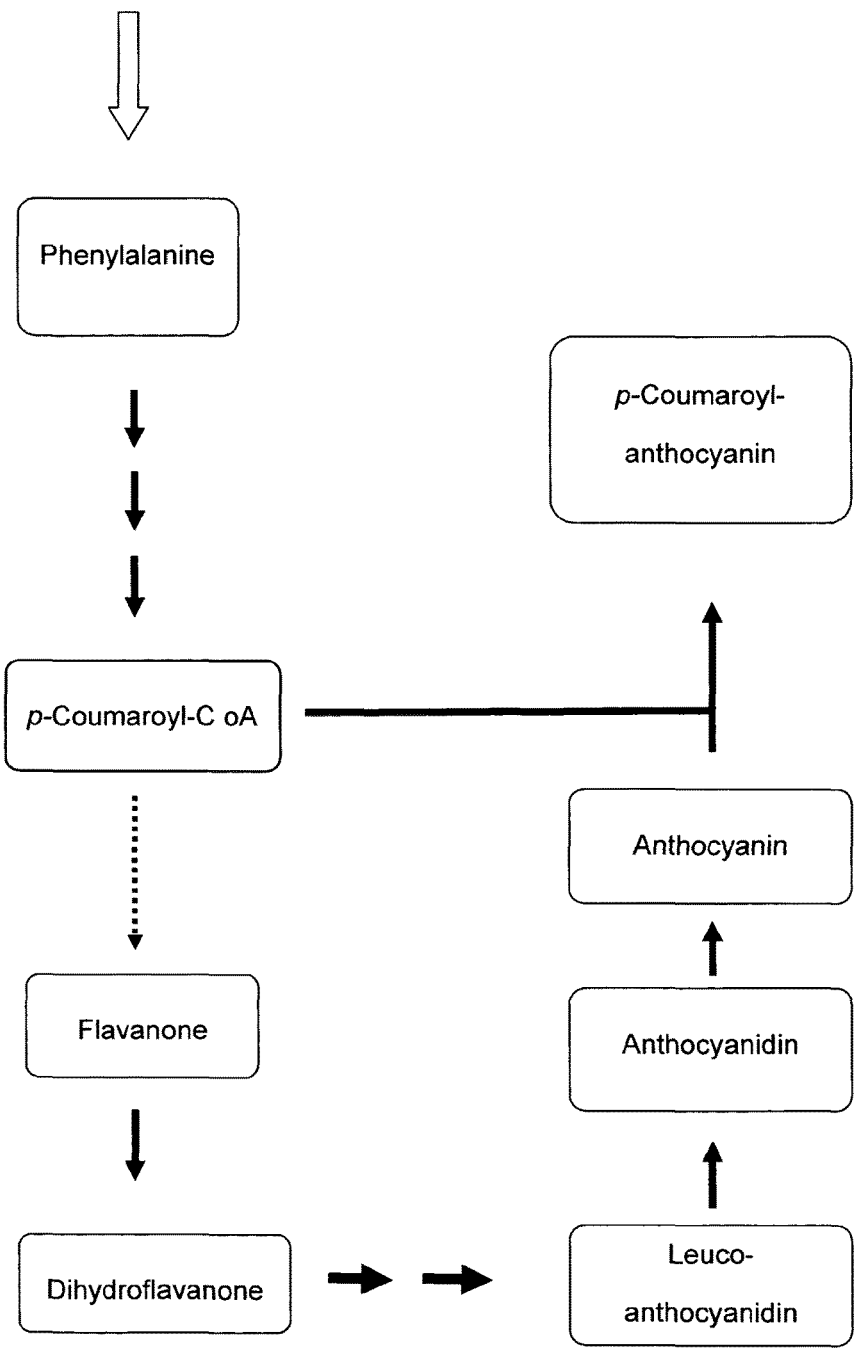
FIG. 3 shows a schematic overview of examples of the pathways to produce anthocyanins according to the invention. In this example a host cell is capable of producing p-Coumaroyl-CoA. With the aid of additional enzymatic steps, the host cell is also capable of producing an anthocyanidin using said p-Coumaroyl-CoA as precursor. The anthocyanidin may be glycosylated by a glycosyltransferase to form anthocyanin and the anthocyanin may be further acylated using p-Coumaroyl-CoA as acyl donor to form p-Coumaroyl-anthocyanin. p-Coumaroyl-anthocyanin is also considered an anthocyanin according to the present invention. A large variety of other acyl donors may be used with the present invention.

A screening platform is a method of identifying anthocyanins with improved stability, color, hue or other properties. In one embodiment, the screening platform comprises isolating one or more anthocyanins from host cells and/or from culture medium of the host cells; exposing the one or more anthocyanins to steadily increasing concentrations of a reagent to effect a change in the color intensity of the one or more anthocyanins, and comparing the concentration where a loss of color intensity occurs with a control, wherein the ability to retain color intensity at higher concentrations of exposure to the reagent than the control indicates improved anthocyanin stability.

One embodiment of the invention provides a method of identifying anthocyanins with improved stability, color, hue or other property using a screening method. The method includes providing one or more host cells capable of producing at least one anthocyanidin, wherein said host cells comprise one or more heterologous glycosyltransferase (GT) nucleic acid molecules, one or more heterologous acyltransferase (AT) nucleic acid molecules, or both one or more heterologous GT nucleic acid molecules and one or more heterologous AT nucleic acid molecules. GT and AT nucleic acid molecules are known in the art. Exemplary GenBank Accession Numbers for GT nucleic acid molecules include, but are not limited to, NM_100432.1, NM_113071.2, NM_113073.2, NM_001134258.1, NM_001142488.1, FJ237534.1, GU584127.1, JQ247689.1, NM_059035.1, NM_067587.1, NM_068512.1, NM_072411.1, NM_071915.1, NM_071659.2, NM_071942.2, NM_001028523.1, NM_072419.2, NM_068511.2, NM_001128946.1, NM_001026585.3, NM_059036.5, NM_059037.4, NM_068530.3, NM_001268558.1, NM_070877.3, NM_070897.4, NM_182348.3, NM_071370.3, NM_071577.6, NM_071873.4, NM_071910.3, NM_071916.6, NM_071968.5, NM_071987.4, NM_072409.5, NM_072410.5, NM_072415.3, NM_182344.3, NM_072417.4, NM_001129369.3, NM_075711.5, NM_076781.3, NM_001083287.3, NM_171786.5, GU299097.1, GU299103.1, GU299105.1, GU299107.1, GU299112.1, GU299114.1, GU299116.1, GU299119.1, GU299125.1, GU299126.1, GU299130.1, GU299143.1, NM_001037428.2, AY735003.1, EF408255.1, EF408256.1, NM_001074.2, NM_152404.3, NM_001171873.1, GU170355.1, GU170356.1, GU170357.1, AF093878.1, NM_153314.2, NM_201425.2, NM_201423.2, NM_012683.2, NM_201424.2, NM_001039549.1, NM_057105.3, NM_130407.2, NM_175846.2, NG_005502.3, NM_001039691.2, NG_005503.6, AB499074.1, AB499075.1, AF091397.1, AF091398.1, KC464461.1, JQ247689.1, FJ236328.1, JX011637.1, GU434222.1, GU170357.1, GU170356.1, GU170354.1, GU170355.1, AB541990.1, AB541989.1, EF408256.1, EF408255.1, NM_113073.2, NM_100435.3, NM_113071.2, NM_100432.1, HM543573.1, GU584127.1, AB499075.1, AB499074.1, AAD29570.1, Q06321.1, AAD29571.1, GT72B1, AB190262, AY345976.1, NM_180266.2 NM_112524.3, BAD29722.1, AF091398.1, AY339370.1, AY345976.1, NM_100021.2, NM_127108.3, NM_100432.1, NM_125350.2, AY345974.1, AY345977.1, NM_121711.4, NM_127890.3, NM_117638.3, NM_129233.1, NM_129235.3, NM_106048.3, AF190634.1, NM_116337.2, NM_119574.3, NM_114533.2, NM_128529.2, NM_127889.1, NM_202156.1, or NM_001247751.1.

Exemplary GenBank Accession Numbers for AT nucleic acid molecules include, but are not limited to A15528.1, XM_815926.1, NM_001157346.1, JQ844755.1, XM_005705471.1, XM_003189876.1, XM_001398618.2, XM_004365862.1, AB242298.1, NM_125509.2, NM_001247490.1, NM_001154098.1, EU979541.1, AB010708.1, AB811449.1, AB267670.1, AB217625.1, AB029340.1, XM_002326074.2, KC876023.1, KC876022.1, KC876021.1, BT006030.1, XM_002531309.1, EU968486.1, EU955836.1, AK118746.1, AY383735.1, AB026494.1, AB267672.1, AB267669.1, AB267668.1, AB267667.1, XM_003638134.1, or AY037199.1.

The host cells are cultivated under conditions allowing growth of said cells and production of at least one anthocyanin thereby. The host cells and/or culture medium are screened for anthocyanins with improved stability, color, hue or other properties. Anthocyanins are thereby identified with improved stability, color, hue or other properties.

The screening can comprise isolating one or more anthocyanins from said host cells and/or from culture medium of the host cells and exposing the one or more anthocyanins to steadily increasing concentrations of a reagent to effect a change in the color intensity of the one or more anthocyanins. The concentration where a loss of color intensity occurs is compared with a control, wherein the ability to retain color intensity at higher concentrations of exposure to the reagent than the control indicates improved or changed anthocyanin stability. The reagent can be a base, a strong base, light, heat, oxygen, lithium hydroxide, sodium hydroxide, potassium hydroxide, rubidium hydroxide, or combinations thereof. The color intensity can be determined by spectrophotometry.

Improved color, hue, stability or other anthocyanin property means improved for any purpose for which one of skill in the art would use an anthocyanin. Therefore, improved stability could mean better stability (resistance to break down) in for example an acid environment. However, it could also mean less stability (more likely to break down) in an acid environment, where, for example, it is desired for the anthocyanin to break down easily (e.g., in the gastrointestinal tract). In one embodiment, an improvement in color, hue or stability or other property means any change in property that occurs as compared to the starting molecule.

Method for Identifying a Host Cell Capable of Producing an Anthocyanin

The present invention provides methods for identifying useful ways of producing an anthocyanin with a desired property, which for example may be any of the properties described herein below in the section "Predetermined property". Thus, the invention enables production of anthocyanins with very diverse properties. In particular, the methods of the invention are not dependent on a whether an anthocyanin with a particular property is available in nature and the methods are also not dependent on collection or cultivation of a large array of different plants.

Rather, the invention is based on the finding that by combining a range of anthocyanidins with a range of acyltransferases and glycosyltransferases, then a large variety of anthocyanin with different properties can be prepared, even outside the natural plant environment. Furthermore, the anthocyanins thus produced may be naturally occurring anthocyanins or they may be anthocyanins, which are otherwise not found in nature.

Thus, the invention relates to methods comprising the steps of:
a. providing at least one anthocyanidin,
b. providing a plurality of glycosyltransferases and/or acyltransferases,
c. contacting the at least one anthocyanidin with various combinations of one or more glycosyltransferases and/or acyltransferases
d. screening for anthocyanins with predetermined properties thereby identifying a method for producing anthocyanins with predetermined or improved properties.

The methods may be performed in a number of different ways. In one embodiment such methods are performed in vitro, for example as described herein below in the section "Method of identifying an incubation mixture for production of an anthocyanin." In another embodiment the methods are performed using a composition of host cells, wherein the host cells are capable of producing at least one anthocyanidin, and wherein the host cells of the composition express different combinations of one more glycosyltransferases and/or acyltransferases. Because the host cells of the composition express different combinations of one more glycosyltransferases and/or acyltransferases, the individual host cells are capable of producing different anthocyanins. Thus host cells producing an anthocyanin of interest may be selected, propagated, and used for production of a particular anthocyanin.

Thus, the invention provides methods of identifying a host cell capable of producing an anthocyanin with a predetermined property or an improved property, said method comprising the steps of:
a. providing a composition of host cells, which may be any of the compositions described herein below in the section "Composition of host cells,"
wherein each host cell is capable of producing at least one anthocyanidin, which may be any of the anthocyanidins described herein below in the section "anthocyanidin;" and
wherein each host cell comprises at least one heterologous nucleic acid molecule selected from the group consisting of heterologous GT nucleic acid molecules and heterologous AT nucleic acid molecules,
wherein each heterologous GT nucleic acid molecule encodes a glycosyltransferase, which may be any of the glycosyltransferases described herein below in the section "Glycosyltransferase," and
wherein each heterologous AT nucleic acid molecule encodes an acyltransferase, which may be any of the acyltransferases described herein below in the section "Acyltransferase,"
wherein at least 2 host cells comprises different heterologous nucleic acid molecules,
b. cultivating the host cells under conditions allowing growth of the cells, for example the host cells can be cultivated as described herein below in the section "Host cells."
c. screening the composition of host cells, for cells producing an anthocyanin with the predetermined property or improved property, wherein said predetermined property may be any of the predetermined properties described herein below in the section "Predetermined properties";
d. selecting said host cell;
thereby identifying a host cell capable of producing an anthocyanin with a predetermined property or improved property.

The screening may be performed in different ways depending on the predetermined or improved properties of the anthocyanin. For example the screening may be performed as described herein below in the section "Predetermined properties". The method may comprise just one screening or several rounds of screening. Frequently, it will be desirable to make more than one screening. For example, the methods may comprise initial screening(s) identifying one or more host cells, which are likely to produce an anthocyanin with the predetermined or improved property. The selected one or more host cells may then be propagated and subjected to further screening(s) identifying one or more host cells, which produces an anthocyanin with the predetermined or improved property. The initial screening(s) may be performed once, or there may be several rounds of initial screenings. Similarly, the further screening may be performed once or several times. The further screening(s) typically test for the same predetermined or improved property as the initial screening using a different method. Frequently, the initial screening may be a high through-put procedure, whereas the second screening may be a more specific screening validating the result of the first screening.

Once one or more host cell(s) producing an anthocyanin with a predetermined or improved property have been identified, these host cell(s) may be used for production of said anthocyanin. It is, however, also comprised within the invention that said host cell(s) may be subjected to further optimization.

In one embodiment, the heterologous nucleic acids of the selected host cell(s), for example the heterologous GT nucleic acid molecules and the heterologous AT nucleic acid molecules comprised in the selected host cell may be purified and said heterologous nucleic acid molecules may then be inserted into a second composition of host cells. Thus, each of the host cells of the second composition may then comprise a subset of the heterologous nucleic acid molecules comprised in the first selected host cell(s). The second population of host cells may also comprise additional heterologous nucleic acid molecules.

The second composition of host cells can then be subjected to one or more screenings for host cells producing an anthocyanin with the predetermined or improved property.

Thus, in one embodiment of the invention the methods for identifying a host cell capable of producing an anthocyanin comprises the further steps of
a. isolating the heterologous GT nucleic acid molecules and/or heterologous AT nucleic acid molecules of the selected host cell(s); and
b. preparing a second composition of host cells, wherein each host cell of the second composition is capable of producing at least one anthocyanidin, and wherein each host cell of the second composition comprises one or more of said isolated heterologous GT nucleic acid molecules and/or heterologous AT nucleic acid molecules (additional heterologous nucleic acid molecules may be introduced into the cells at this point if desired);

c. performing steps b. to d. with said second composition of host cells.

d. cultivating the host cells under conditions allowing growth of the cells, for example the host cells can be cultivated as described herein below in the section "Host cells."

e. screening the composition of host cells, for cells producing an anthocyanin with the predetermined property or improved property, wherein said predetermined property may be any of the predetermined properties described herein below in the section "Predetermined properties";

f. selecting said host cell;

g. thereby identifying a host cell capable of producing an anthocyanin with a predetermined property or improved property.

These further steps may be repeated as often as desired.

Once one or more host cell(s) producing the anthocyanin with the predetermined or improved properties has been selected, they may be propagated under conditions suitable for propagating that particular type of host cell. They may then be used in methods for producing the anthocyanin as described herein below in the section "Method for producing an anthocyanin."

Another embodiment of the invention provides a method of identifying a host cell capable of producing an anthocyanin with a predetermined or improved property. The method comprises providing a composition of host cells, wherein each host cell is capable of producing at least one anthocyanidin, and wherein each host cell comprises one or more heterologous GT nucleic acid molecules, one or more heterologous AT nucleic acid molecules, or both one or more heterologous GT nucleic acid molecules and one or more heterologous AT nucleic acid molecules. The host cells are cultivated under conditions allowing growth of said host cells and production of at least one anthocyanin thereby. The composition of host cells is screened for host cells producing an anthocyanin with the predetermined property. A host cell is selected such that a host cell capable of producing an anthocyanin with a predetermined or improved property is identified.

Method of Identifying an Incubation Mixture for Production of an Anthocyanin

As described above, it is one aspect of the present invention to provide methods for production of an anthocyanin with a predetermined or improved property.

In one embodiment said methods may be in vitro methods, for example, the methods can be methods for identifying useful combinations of glycosyltransferases and/or acyltransferases for preparing an anthocyanin with a predetermined or improved property.

For example, the invention provides methods of identifying an incubation mixture for production of an anthocyanin with a predetermined or improved property, wherein the methods comprises the steps of:

a. providing a selection of incubation mixtures, wherein each incubation mixture comprises at least one anthocyanidin, which may be any of the anthocyanidins described herein below in the section "Anthocyanidins" at least one sugar donor, which may be any of the sugar donors described herein below in the section "Glycosyltransferase" at least one acyl donor, which may be any of the acyl donors described herein below in the section "Acyl donor," one or more glycosyltransferases and/or acyltransferases, which may be any of the glycosyltransferases described herein below in the section "Glycosyltransferase" and/or any of the acyltransferases described herein below in the section "Acyltransferases", wherein at least two incubation mixtures comprises a different combination of glycosyltransferases and/or acyltransferases;

b. incubating said incubation mixture under conditions allowing for activity of said glycosyltransferase and/or acyltransferase, c. screening the selection for incubation mixtures comprising an anthocyanin with the predetermined or improved property, wherein the predetermined property may be any of the predetermined properties described herein below in the section "Predetermined property";

d. selecting said incubation mixture;

thereby identifying an incubation mixture useful for producing an anthocyanin with a predetermined or improved property.

In one embodiment of the invention each incubation mixture comprises a plurality of enzymes selected from the group consisting of glycosyltransferases and acyltransferases. Thus, each incubation mixture may comprise at least 5, such as at least 10, for example at least 15, such as at least 20 different enzymes selected from the group consisting of glycosyltransferases and acyltransferases. For example, the incubation mixture may comprise at least 2, such as at least 5, for example at least 10 different glycosyltransferases and at least 2, such as at least 5, for example at least 10 different acyltransferases.

The screening can be performed in different ways depending on the predetermined or improved properties of the anthocyanin. For example the screening may be performed as described herein below in the section "Predetermined properties". The method may comprise just one screening or several rounds of screening. Sometimes more than one screening is performed. For example the methods may comprise initial screening(s) identifying one or more incubation mixtures, which are likely to produce an anthocyanin with the predetermined or improved property. The selected one or more incubation mixtures can then be subjected to further screening(s) identifying one or more incubation mixtures, which produces an anthocyanin with the predetermined or improved property. The initial screening(s) can be performed once, or there can be several rounds of initial screenings. Similarly, the further screening can be performed once or several times. The further screening(s) typically test for the same predetermined or improved property as the initial screening using a different method. Frequently, the initial screening can be a high through-put procedure, whereas the second screening may be a more specific screening validating the result of the first screening.

Once a suitable incubation mixture has been selected, a mixture containing the same anthocyanidin(s), sugar donor(s), acyl donor(s), glycosyltransferase(s) and acyltransferase(s) can then be employed for the production of an anthocyanidin with a predetermined property. The selected incubation mixture(s) may be subjected to further optimization.

In one embodiment, the methods further comprise identification of which glycosyltransferases and/or acyltransferases are contained within the selected incubation mixture. This can, for example, be accomplished by prior registration of which glycosyltransferases and/or acyltransferases are comprised in which incubation mixture. It is also possible to identify the glycosyltransferases and/or acyltransferases by purification and analytical methods.

Once the glycosyltransferases and/or acyltransferases contained within the selected incubation mixture(s) are identified a second selection of incubation mixtures can be prepared. Each of the incubation mixtures of the second selection of incubation mixtures comprises a subset of the identified glycosyltransferases and/or acyltransferases and furthermore at least one anthocyanidin, at least one acyl donor and at least one sugar donor.

The second selection of incubation mixtures can then be subjected to one or more screenings for host cells producing an anthocyanin with the predetermined or improved property.

Thus, in one embodiment of the invention the methods for identifying an incubation mixture capable of producing an anthocyanin comprises the further steps of
a. identifying the glycosyltransferases and/or acyltransferases contained in the selected incubation mixture;
b. preparing a second selection of incubation mixtures, wherein each incubation mixture comprises
at least one anthocyanidin, which may be any of the anthocyanidins described herein below in the section "Anthocyanidins,"
at least one sugar donor, which may be any of the sugar donors described herein below in the section "Glycosyltransferase,"
at least one acyl donor, which may be any of the acyl donors described herein below in the section "Acyl donor."
one or more of the identified glycosyltransferases and/or acyltransferase (one or more additional GTs or ATs may be added to the incubation mixture at this point)
c. performing steps b. to d. with said second selection of incubation mixtures.
d. incubating said incubation mixture under conditions allowing for activity of said glycosyltransferase and/or acyltransferase,
e. screening the selection for incubation mixtures comprising an anthocyanin with the predetermined or improved property, wherein the predetermined property may be any of the predetermined properties described herein below in the section "Predetermined property";
f. selecting said incubation mixture.
These further steps may be repeated as often as desired.

Once one or more incubation mixtures producing the anthocyanin with the predetermined or improved properties have been selected, an incubation mixture containing the same anthocyanidin, acyl donor, sugar donor, glycosyltransferase(s) and acyltransferase(s) can be used in methods for producing the anthocyanin as described herein below in the section "Method for producing an anthocyanin."

Method for Producing an Anthocyanin

The present invention also provides methods of producing an anthocyanin, and in particular the invention provides methods of producing an anthocyanin with a predetermined property or improved property such as stability, color or hue.

In one embodiment, the invention provides a method of producing anthocyanins with a predetermined property or improved property such as stability, color, or hue or combinations thereof. The method comprises providing two or more (e.g., 2, 5, 10, 100, 500, 1,000, 10,000, or more) host cells capable of producing at least one anthocyanidin, wherein each host cell comprises one or more heterologous GT nucleic acid molecules and one or more heterologous AT nucleic acid molecules. The host cells are cultivated under conditions allowing growth of the host cells and production of anthocyanins thereby. One or more anthocyanins with a predetermined property or improved property such as improved color, improved stability, and/or improved hue are isolated from the host cells and/or from the culture medium.

The host cell can be any host cell capable of producing an anthocyanin of interest. The host cell can be a host cell identified by the methods described by the present invention.

The invention also provides methods of producing an anthocyanin, said method comprising the steps of:
a. providing an incubation mixture comprising:
at least one anthocyanidin, which may be any of the anthocyanidins described herein below in the section "Anthocyanidin,"
at least one sugar donor, which may be any of the sugar donors described herein below in the section "Glycosyltransferase,"
at least one acyl donor, which may be any of the acyl donors described herein below in the section "Acyl donor," and
at least two enzymes selected from the group consisting of glycosyltransferases and acyltransferases, which may be any of the glycosyltransferases described herein below in the section "Glycosyltransferases" and any of the acyltransferases described herein below in the section "Acyltransferase", and
b. incubating said incubation mixture under conditions allowing for activity of said enzymes,
c. optionally isolating the anthocyanin from the incubation mixture.

The incubation mixture can be any incubation mixture capable of producing an anthocyanin with the predetermined or improved properties, however, the incubation mixture can be an incubation mixture identified by the methods of invention described herein.

Heterologous Nucleic Acid Molecules

The host cells to be used with the invention can comprise a plurality of different heterologous nucleic acid molecules. In order to be able to distinguish different kinds of heterologous nucleic acid molecules, different designations are used for the different heterologous nucleic acid molecules.

The term "heterologous nucleic acid molecule" as used herein refers to a nucleic acid molecule, which is not present naturally in a host cell. Thus, typically a heterologous nucleic acid has been inserted into a host cell using recombinant technology. Heterologous nucleic acid molecules encoding a polypeptide are in general operably linked to a nucleic acid molecule directing expression of said heterologous nucleic acid in the host cell. Said nucleic acid molecule directing expression of said heterologous nucleic acid in the host cell may for example comprise a promoter molecule.

A promoter is a region of DNA that facilitates the transcription of a particular polynucleotide. Promoters are located near the polynucleotides they regulate, on the same strand and typically upstream (towards the 5' region of the sense strand). In order for the transcription to take place, the enzyme that synthesizes RNA, known as RNA polymerase, must attach to the DNA near a gene. Promoters contain specific DNA molecules and response elements that provide a secure initial binding site for RNA polymerase and for proteins called transcription factors that recruit RNA polymerase. These transcription factors have specific activator or repressor molecules of corresponding nucleotides that attach to specific promoters and regulate gene expressions.

The promoter nucleic acid molecule can in general be positioned immediately adjacent to the coding heterologous nucleic acid molecule.

The promoter nucleic acid molecule according to the present invention in general comprises at least a core promoter, which is the minimal portion of the promoter required to properly initiate transcription. In addition the promoter nucleic acid molecule may comprise one or more of the following promoter elements:

Transcription Start Site (TSS)
A binding site for RNA polymerase
General transcription factor binding sites
Proximal promoter molecule upstream of the gene that tends to contain primary regulatory elements
Specific transcription factor binding sites
distal promoter molecule upstream of the gene that may contain additional regulatory elements, often with a weaker influence than the proximal promoter and/or
Binding sites for repressor proteins.

As used herein the term "heterologous GT nucleic acid molecule" refers to a heterologous nucleic acids molecule encoding a glycosyltransferase, which may be any of the glycosyltransferases described herein below in the section "Glycosyltransferase."

As used herein the term "heterologous AT nucleic acid molecule" refers to a heterologous nucleic acid molecule encoding an acyltransferase, which may be any of the acyltransferases described herein below in the section "Acyltransferase."

As used herein the term "heterologous enzyme nucleic acid molecule" refers to a heterologous nucleic acid molecule encoding an enzyme involved in a biosynthesis pathway. In particular "heterologous enzyme nucleic acid molecule" may be heterologous nucleic acid molecules encoding an enzyme involved in the biosynthesis pathway for a compounds selected from the group consisting of acyl donors (such as any of the acyl donors described herein below in the section "Acyl donors," flavanones and anthocyanidins (such as any of the anthocyanidins described herein below in the section "Anthocyanidin."

Anthocyanin

The term "anthocyanin" as used herein refers to any anthocyanidin, which have been glycosylated and/or acylated at least once. However, an anthocyanin may also have been glycosylated and/or acylated several times. Thus, in principle, an anthocyanin may also be an anthocyanin, which has been glycosylated and/or acylated at least once.

Thus, an anthocyanin may be any of the anthocyanidins described herein below, wherein said anthocyanidin are substituted with one or more selected from the group consisting of glycosyl, acyl, substituents consisting of more than one glycosyl, substituents consisting of more than one acyl and substituents consisting of one or more glycosyl(s) and one or more acyl(s).

The anthocyanidin can be substituted at any useful position. Frequently the anthocyanidin is substituted at one or more of the following positions: the 3 position on the C-ring, the 5 position on the A-ring, the 7 position on the A ring, the 3' position of the B ring, the 4' position of the B-ring or the 5' position of the B-ring.

Accordingly, in one embodiment of the invention the anthocyanin is a compound of the formula I

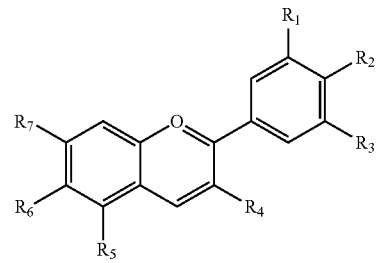

(I)

wherein $R_1$ is selected from the group consisting of —H, —OH, —OCH$_3$ and O—R$_8$; and $R_2$ is selected from the group consisting of —H, —OH and O—R$_8$; and $R_3$ is selected from the group consisting of —H, —OH, —OCH$_3$ and O—R$_8$; and $R_4$ is selected from the group consisting of —H, —OH and O—R$_8$; and $R_5$ is selected from the group consisting of —OH, —OCH$_3$ and O—R$_8$; and $R_6$ is selected from the group consisting of —H and —OH; and $R_7$ is selected from the group consisting of —OH, —OCH$_3$ and O—R$_8$ and $R_8$ is selected from the group consisting of glycosyl, acyl, substituents consisting of more than one glycosyl, substituents consisting of more than one acyl and substituents consisting of one or more glycosyl(s) and one or more acyl(s); and wherein at least one of $R_1$, $R_2$, $R_3$, $R_4$, $R_5$ and $R_7$ is —O—R$_8$.

In particular, the anthocyanin may be a compound of formula I, wherein $R_1$ is selected from the group consisting of —H, —OH, and —OCH$_3$; and $R_2$ is selected from the group consisting of —H and —OH; and $R_3$ is selected from the group consisting of —H, —OH and —OCH$_3$; and $R_4$ is selected from the group consisting of —H, —OH and O—R$_8$; and $R_5$ is selected from the group consisting of —OH, —OCH$_3$ and O—R$_8$; and $R_6$ is selected from the group consisting of —H and —OH; and $R_7$ is selected from the group consisting of —OH, —OCH$_3$ and O—R$_8$ and $R_8$ is selected from the group consisting of glycosyl, acyl, substituents consisting of more than one glycosyl, substituents consisting of more than one acyl and substituents consisting of one or more glycosyl(s) and one or more acyl(s), and wherein at least one of $R_4$, $R_5$ and $R_7$ is —O—R$_8$.

Furthermore, the anthocyanin may be a compound of formula I, wherein $R_1$ is selected from the group consisting of —H, —OH, and —OCH$_3$; and $R_2$ is selected from the group consisting of —H and —OH; and $R_3$ is selected from the group consisting of —H, —OH and —OCH$_3$; and $R_4$ is selected from the group consisting of O—R$_8$; and $R_5$ is selected from the group consisting of —OH and —OCH$_3$; and $R_6$ is selected from the group consisting of —H and —OH; and $R_7$ is selected from the group consisting of —OH and —OCH$_3$ and $R_8$ is selected from the group consisting of glycosyl, acyl, substituents consisting of more than one glycosyl, substituents consisting of more than one acyl and substituents consisting of one or more glycosyl(s) and one or more acyl(s).

The acyl may be any acyl. In one embodiment one or more acyls are selected from the group consisting of the acyl moiety of a fatty acid. In another embodiment one or more acyls are selected from the group consisting of coumaroyl, benzoyl, sinapoyl, feruloyl and caffeoyl, malonyl and hydroxybenzoyl.

The glycoside can be any sugar residue. For example, one or more glycosides may be selected from the group consisting of glucoside, rhamnoside, xyloside, galactoside and arabinoside.

The substituent consisting of one or more glycosides can, for example, be a monosaccharide, disaccharide or a trisaccharide. The monosaccharide may for example be selected from the group consisting of glucoside, rhamnoside, xyloside, galactoside and arabinoside. The disaccharide and the trisaccharide may for example consist of glycosides selected from the group consisting of glucoside, rhamnoside, xyloside, galactoside and arabinoside.

The substituent consisting of one or more glycosides and one or more acyl may for example be a monosaccharide, disaccharide or a trisaccharide substituted at one or more positions with an acyl. The substituent consisting of one or more glycosides and one or more acyl may for example be may for example be a monosaccharide selected from the group consisting of glucoside, rhamnoside, xyloside, galactoside and arabinoside, wherein any of the aforementioned can be substituted at one or more positions with an acyl selected from the group consisting of coumaroyl, benzoyl, sinapoyl, feruloyl and caffeoyl, malonyl and hydroxybenzoyl. The substituent consisting of one or more glycosides and one or more acyl may also for example be a disaccharide or a trisaccharide consisting of glycosides selected from the group consisting of glucoside, rhamnoside, xyloside, galactoside and arabinoside, wherein any of the aforementioned can be substituted at one or more positions with an acyl selected from the group consisting of coumaroyl, benzoyl, sinapoyl, feruloyl and caffeoyl, malonyl and hydroxybenzoyl.

In one embodiment of the invention an anthocyanin can be multiply glycosylated. Such anthocyanins have improved systemic bioavailability (compared to the aglycon (a non-glycosylated molecule) alone or an anthocyanin with fewer glycosylations). The sugars can be removed in the GI tract. Such multiply glycosylated anthocyanins (one or more glycosylations) also have improved aqueous solubility.

The improvement of bioavailability or solubility or a combination thereof can be 2, 5, 10, 50, 100, 200 or more fold.

The systematic bioavailability of an orally delivered anthocyanin can be improved by adding one or more sugar units to the anthocyanin. The improved anthocyanin can be ingested. The sugars can be fully or partially removed in the GI tract. The anthocyanin with no sugars or fewer sugars than when ingested can then cross through the GI wall.

The solubility of an anthocyanin can be improved by adding more than one sugar unit to the anthocyanin.

The sugars can be added to the anthocyanin by an enzyme or by a metabolic process within a cell. Production of these anthocyanins can be by fermentation in a cell, such as a yeast or bacterial cell. The sugars can be any sugar, for example, glucose, galactose, lactose, fructose, maltose, and can be added to one or more than one site on the anthocyanin. There can be more one sugar per site, or 2, 3, 4, 5, or more sugars per site. The anthocyanin can first be derivatized with a group (e.g., P450 or other enzyme) that the sugar is subsequently added to.

Anthocyanins can exist in at least four different pH-dependent chemical forms, namely, flavylium ion (A), hemiketals (E), quinoid bases (B) and chalcones (F), arising at pH 1-3, 4-5, 6-8 and 7-8, respectively. At more alkaline pH values, anthocyanins have consistently been shown to degrade to their constituent phenolic acids. Note that the hemiketal (E) is the anthocyanin plus OH. The quinoid base (B) is the anthocyanin minus OH. If protection of these forms was desired, the concept of chemical isoforms may need to be clarified. Spectrophotometric quantification of anthocyanins is typically performed at a pH titration of 1 (colored) to 4.5 (colorless).

Co-pigmentation can affect stability, color, and hue. This can be an intramolecular interaction e.g. of the acyl group with the rest of the anthocyanin molecule or intermolecular interactions with other molecules in solution. The effect of acyl group variation protects intramolecular but not intermolecular co-pigmentation.

For processing, formulation and storage of products containing anthocyanins, stabilization of the intact anthocyanin is desired. However, in vivo therapeutic effects of anthocyanins can be due to one of more of native anthocyanin, degradation products, metabolites or anthocyanin derivatives. Notably, the amount of native anthocyanin in plasma has been quoted as less than 1% of the consumed quantities. This has been considered to be due to limited intestinal absorption, high rates of cellular uptake, metabolism and excretion.

Therefore, for therapeutic applications of anthocyanins, it can be advantageous to use anthocyanins with instability at the relevant stage of the digestive tract, or derivatization for maximum adsorption at the relevant stage of the digestive tract. Colonic metabolism of anthocyanins can also be considered. Therefore, in some instances "improved stability" of an anthocyanin may actually be a decrease in stability for delivery to a specific stage of the digestive tract or colon. The chemical forms of anthocyanins ingested in the diet may not be the ones that reach microbiota but instead their respective metabolites that were excreted in the bile and/or from the enterohepatic circulation.

Predetermined Property

The present invention relates to anthocyanins with a predetermined property and methods of identifying production methods for such anthocyanins.

The predetermined property may in particular be selected from the group consisting of color, hue and chemical stability against factors such as pH, light, heat, and oxygen concentration.

In particular the predetermined property may be a particular color. The color may be any color, but in particular the color may be a color in the red, purple and blue spectrum. In embodiments of the invention employing use of host cells where the predetermined property is a particular color, then the screening can be a screening for host cell having the particular color. This may be done in an automated manner.

In particular, the initial screening can be a screening for host cells having the particular color. The further screening can involve purification of the anthocyanin from the host cell and determination of the color. In embodiments of the invention employing use of incubation mixtures where the predetermined property is a particular color, then the screening can be a screening for an incubation mixture having the particular color. This may be done in an automated manner.

Similarly, the predetermined property can be a particular hue. In embodiments of the invention employing use of host cells where the predetermined property is a particular hue, then the screening can be a screening for host cell having the particular hue. This may be done in an automated manner. In particular, the initial screening can be a screening for host cells having the particular hue. The further screening can involve purification of the anthocyanin from the host cell and determination of the hue. In embodiments of the invention employing use of incubation mixtures where the predetermined property is a particular hue, then the screening may be a screening for an incubation mixture having the particular hue. This may be done in an automated manner.

It is one aspect of the invention to provide methods for identifying a host cell capable of producing an anthocyanin with a predetermined color and/or hue, said method comprising the steps of:

a. providing a composition of host cells, which may be any of the compositions of host cells described herein below in the section "Composition of Host cells,"
   wherein each host cell is capable of producing at least one anthocyanidin, which may be any of the anthocyanidins described herein below in the section anthocyanidin, and
   wherein each host cell comprises an expressible heterologous nucleic acid molecule, wherein each expressible heterologous nucleic acid molecule encodes an enzyme selected from the group consisting of glycosyltransferases and acyltransferases, which may be any of the glycosyltransferases described herein below in the section "Glycosyltransferases" and any of the acyltransferases described herein below in the section "Acyltransferases," and
   wherein at least 2 host cells comprise different expressible heterologous nucleic acid molecules,
b. cultivating said host cells under conditions allowing growth of said cells
c. screening the composition of host cells, for cells having the predetermined color and/or hue;
d. selecting said host cell having said predetermined color and/or hue; thereby identifying a host cell capable of producing an anthocyanin with a predetermined color and/or hue.

Anthocyanidin

The methods of the invention can, for example, involve use of an incubation mixture comprising an anthocyanidin or use of a host cell capable of producing an anthocyanidin.

Said anthocyanidin may be any anthocyanidin available to the skilled person. In one embodiment of the invention, the anthocyanidin is a compound of the formula I

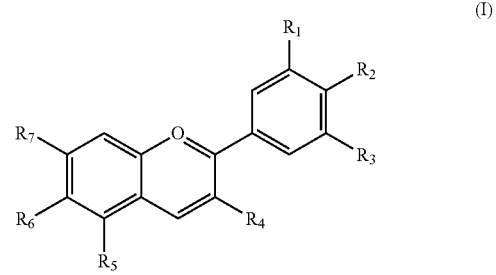

wherein
$R_1$ is selected from the group consisting of —H, —OH and —OCH$_3$; and
$R_2$ is selected from the group consisting of —H and —OH; and
$R_3$ is selected from the group consisting of —H, —OH and —OCH$_3$; and
$R_4$ is selected from the group consisting of —H and —OH; and
$R_5$ is selected from the group consisting of —OH and —OCH$_3$; and
$R_6$ is selected from the group consisting of —H and —OH; and
$R_7$ is selected from the group consisting of —OH and —OCH$_3$ For example, the anthocyanidin may be selected from the group consisting of aurantinidin, cyanidin, delphinidin, europinidin, luteolinidin, pelargonidin, malvidin, peonidin, petunidin and rosinidin.

In embodiments of the invention relating to use of a host cell, said host cell in general is capable of producing at least one anthocyanidin. Therefore, the host cell can express enzymes of the biosynthesis of said anthocyanidins. In is possible that the host cell expresses such enzymes naturally. This may in particular be the case when the host cell is a cell of plant origin. However, in embodiments of the invention where the host cell is a yeast or bacterial cell, then generally it will be required that the yeast or bacterial cell contains one or more heterologous enzyme nucleic acid molecules encoding enzymes of the biosynthesis pathway leading to one or more anthocyanidins.

The host cells to be used with the invention are capable of producing one or more flavanones (e.g., naringenin, butin, dihydrotricetin, eriodictyol, hesperetin, hesperidin, homoeriodictyol, isosakuranetin, naringin, pinocembrin, poncirin, sakuranetin, sakuranin, sterubin). In order to achieve this it may be required that the host cell contains one or more heterologous enzyme nucleic acid molecules as described herein below in the section "Flavanones."

Thus, with reference to FIG. 1 the host cell can be capable of performing step 1 and step 2 as shown in the figure. It is described in more detail herein below how host cells may be modified to be able to perform steps 1 and 2.

The host cell can be capable of producing an anthocyanidin from naringenin or other flavanone. With reference to FIG. 1 the host cell can be capable of performing step 3.

Several biosynthesis pathways for conversion of flavanone such as naringenin to an anthocyanidin are known. Where the host cell is a yeast or bacterial cell the host cell can comprise heterologous enzyme nucleic acid molecules encoding one or more enzymes of the biosynthesis pathway for conversion of a flavanone such as naringenin to an anthocyanidin. The host cell can comprise heterologous enzyme nucleic acid molecules encoding all the enzymes of the biosynthesis pathway for conversion of a flavanone such as naringenin to an anthocyanidin.

Thus, the host cell can comprise heterologous enzyme nucleic acid molecules encoding one or more enzymes of the biosynthesis pathway for conversion of naringenin to aurantinidin. For example the host cell can comprise heterologous enzyme nucleic acid molecules encoding all the enzymes of the biosynthesis pathway for conversion of naringenin to aurantinidin.

The host cell can also comprise heterologous enzyme nucleic acid molecules encoding one or more enzymes of the biosynthesis pathway for conversion of naringenin to delphinidin. For example the host cell may comprise heterologous enzyme nucleic acid molecules encoding all the enzymes of the biosynthesis pathway for conversion of naringenin to delphinidin.

The host cell can also comprise heterologous enzyme nucleic acid molecules encoding one or more enzymes of the biosynthesis pathway for conversion of naringenin to europinidin. For example the host cell may comprise heterologous enzyme nucleic acid molecules encoding all the enzymes of the biosynthesis pathway for conversion of naringenin to europinidin.

The host cell can also comprise heterologous enzyme nucleic acid molecules encoding one or more enzymes of the biosynthesis pathway for conversion of naringenin to luteolinidin. For example the host cell can comprise heterologous enzyme nucleic acid molecules encoding all the enzymes of the biosynthesis pathway for conversion of naringenin to luteolinidin.

The host cell can also comprise heterologous enzyme nucleic acid molecules encoding one or more enzymes of the biosynthesis pathway for conversion of naringenin to pelargonidin. For example the host cell can comprise heterologous enzyme nucleic acid molecules encoding all the enzymes of the biosynthesis pathway for conversion of naringenin to pelargonidin.

The host cell can also comprise heterologous enzyme nucleic acid molecules encoding one or more enzymes of the biosynthesis pathway for conversion of naringenin to malvidin. For example the host cell can comprise heterologous enzyme nucleic acid molecules encoding all the enzymes of the biosynthesis pathway for conversion of naringenin to malvidin.

The host cell can also comprise heterologous enzyme nucleic acid molecules encoding one or more enzymes of the biosynthesis pathway for conversion of naringenin to peonidin. For example the host cell can comprise heterologous enzyme nucleic acid molecules encoding all the enzymes of the biosynthesis pathway for conversion of naringenin to peonidin.

The host cell can also comprise heterologous enzyme nucleic acid molecules encoding one or more enzymes of the biosynthesis pathway for conversion of naringenin to petunidin. For example the host cell can comprise heterologous enzyme nucleic acid molecules encoding all the enzymes of the biosynthesis pathway for conversion of naringenin to petunidin.

The host cell can also comprise heterologous enzyme nucleic acid molecules encoding one or more enzymes of the biosynthesis pathway for conversion of naringenin to rosinidin. For example the host cell can comprise heterologous enzyme nucleic acid molecules encoding all the enzymes of the biosynthesis pathway for conversion of naringenin to rosinidin.

The host cell can also comprise heterologous enzyme nucleic acid molecules encoding one or more enzymes of the biosynthesis pathway for conversion of naringenin to cyanidin. For example the host cell can comprise heterologous enzyme nucleic acid molecules encoding all the enzymes of the biosynthesis pathway for conversion of naringenin to cyanidin.

In particular a host cell can comprise one or more of the following heterologous enzyme nucleic acid molecules, such as at least two of, such as least three of, for example at least four of, more or all of the following heterologous enzyme nucleic acid molecules: flavanone 3-dioxygenase (GenBank Accession Numbers, e.g., NM_001281105.1, EU977177.1, NM_001112225.1, or NM_114983.3), flavonoid 3'-monooxygenase (GenBank Accession Numbers, e.g., NM_120881.2, GU990527.1, or XM_003624745.1), flavonoid 3',5'-hydroxylase (GenBank Accession Numbers, e.g., GQ891056.1, NM_001249703.1, or HM011055.1), bifunctional dihydroflavonol 4-reductase/flavanone 4-reductase (GenBank Accession Numbers, e.g., XM_002267131.2, or XM_002268286.2), dihydroflavanol 4-reductase (GenBank Accession Numbers, e.g., AB185901.1 or GU990528.1), leucoanthocyanidin reductase (GenBank Accession Numbers, e.g., NM_001280958.1, NM_001281160.1, or NM_001155409.1), leucoanthocyanidin dioxygenase (GenBank Accession Numbers, e.g., NM_001281218.1, NM_001036623.1, or FJ645769.1), and/or anthocyanidin reductase (ANR) (GenBank Accession Numbers, e.g., NM_001280956.1, NM_104854.3, or AY750963.1).

Glycosyltransferase

The glycosyltransferases to be used with the present invention can be any enzymes that are capable of catalyzing transfer of one monosaccharide residue to acceptor molecules. In particular, the glycosyltransferases to be used with the present invention can be any enzymes that are capable of catalysing transfer of one monosaccharide residue from a sugar donor to acceptor molecules. In particular, the glycosyltransferase to be used with the present invention can be any enzymes that are capable of catalyzing transfer of one monosaccharide residue selected from the group consisting of glucose, rhamnose, xylose, galactose and arabinose to an acceptor molecule selected from the group consisting of anthocyanins and anthocyanidins.

The sugar donor can be any moiety comprising a monosaccharide, such as any donor moiety covalently coupled to a glycoside, such as a glycoside selected from the group consisting of glucoside, rhamnoside, xyloside, galactoside and arabinoside. The donor moiety can, for example, be a nucleotide, such as a nucleoside diphosphate, for example UDP. Thus, the sugar donor can, for example, be the UDP-glycoside, wherein glycoside for example may be selected from the group consisting of glucoside, rhamnoside, xyloside, galactoside and arabinoside.

The art describes a number of glycosyltransferases that can glycosylate compounds of interest. Based on DNA sequence homology of the sequenced genome of the plant *Arabidopsis thaliana* it is believed to contain around 100 different glycosyltransferases. These and numerous others have been analyzed in Paquette, S. et al, Phytochemistry 62 (2003) 399-413. FIG. 1 of this article is a so-called multi-organism tree providing names of numerous suitable glycosyltransferases.

WO01/07631, WO01/40491 and (Arend, J et al., Biotech. & Bioeng (2001) 78:126-131) also describe useful glycosyltransferases, which may be employed with the present invention.

Furthermore, numerous suitable nucleic acid molecules of glycosyltransferases may be found on the Carbohydrate-Active enZYmes (CAZY) database. On the filing date on the present invention the web link for this CAZY database was http://www.cazy.org/.

In the CAZY database, there can be found suitable glycosyltransferase molecules from virtually all species including, animal, insects, plants and microorganisms.

Accordingly, the skilled person has at their disposal a number of different glycosyltransferases capable of glycosylating numerous acceptor molecules.

In one embodiment, one or more glycosyltransferases, for example at least 50% of the glycosyltransferases, such as at least 75% of the glycosyltransferases, such as all glycosyltransferases to be used with the methods of the invention belong to the CAZy family GT1. The skilled person will be able to identify whether a given glycosyltransferase belong to a particular CAZy family using conventional, computer aided methods based mainly on sequence information. The GT1 family comprises at least 5217 genes coding for glycosyltransferases. They are referred to as UGTs and are numbered UGT<family number><group letter><enzyme number>.

Glycosyltransferases that are more than 40% identical to a given GT1 member in amino acid sequence are classified to the same UGT-family within GT1. Those that are 60% or more identical receive the same group letter, and the individual glycosyltransferase is then assigned an enzyme number.

In the art it is thus known how to infer catalytic function or biological role from this classification.

In one embodiment one or more glycosyltransferases, for example at least 50% of the glycosyltransferases, such as at least 75% of the glycosyltransferases, such as all glycosyltransferases to be used with the methods of the invention are UDP-Glycoside:Aglycon-Glucosyltransferase (UGT). UGTs have been identified in plants, animals, fungi, bacteria and viruses. These glycosyltransferases are characterized by utilization of UDP-glycoside as the sugar donor and contain a conserved UGT-defining sequence motif near the C-terminus. In particular, at least 50% of the glycosyltransferases, such as at least 75% of the glycosyltransferases, such as all glycosyltransferases to be used with the methods of the invention can belong to the UDPG-glycosyltransferase family as defined by Paquette, S. et al, Phytochemistry 62 (2003) 399-413.

In embodiments of the invention where a glycosyltransferase enzyme is used, it can, for example, be produced by a host cell, and it can be used in a purified form or as a crude extract from said host cell. The host cell may naturally express said glycosyltransferase. Alternatively, a polynucleotide encoding the glycosyltransferase as described herein can be introduced into the host cell to make a cell wherein the cell expresses a heterologous glycosyltransferase.

Below are described suitable assays to measure the activity of a glycosyltransferase of interest. The assays can be employed to identify glycosyltransferases useful for the methods of the invention.

The ability of a glycosyltransferase to conjugate a monosaccharide to an anthocyanin or an anthocyanidin of interest can for example be determined in an assay comprising the following steps.
  a) incubation of a reaction mixture comprising $^{14}$C-UDP-glycoside, anthocyanin/anthocyanidin and glycosyltransferase at 30° C. between 2 minutes and 2 hours,
  b) terminating the reaction, and
  c) chemical identification and quantification of radioactive product.

Typically, the reaction mixture has a volume of 5 to 2000 μl, but it can be 20 μl and it can include 10-200 mM TrisHCl (pH 7.9); 1-5 μM $^{14}$C-UDP-glycoside (about 11.0 GBq mmol-1); 0-20 mM anthocyanin/anthocyanidin; 25 mM γ-gluconolactone; 0-2 μg/μl BSA and 0-10 ng/μl glycosyltransferase. β-glucosidase inhibitors other than γ-gluconolactone and protein stabilizers other than BSA may be included as appropriate. One possibility to terminate the reaction is to acidify the reaction mixture for example by adding 1/10 volume of 10% acetic acid.

Chemical identification and quantification of the anthocyanin formed in the reaction mixture can be achieved using a variety of methodologies including NMR spectroscopy, TLC analysis, HPLC analyses or GLC analysis in proper combinations with mass spectrometric analysis.

Acyltransferase

The acyltransferases to be used with the present invention can be any enzymes that are capable of catalysing transfer of an acyl residue to acceptor molecules. In particular, the acyltransferases to be used with the present invention can be any enzymes that are capable of catalyzing transfer of acyl residue from an acyl donor to acceptor molecules. In particular, the acyltransferase to be used with the present invention can be any enzymes that are capable of catalyzing transfer of one acyl residue from an acyl donor to an acceptor molecule selected from the group consisting of anthocyanins and anthocyanidins.

The acyltransferase can be any enzyme that is capable of catalyzing transfer of one acyl residue from coenzyme A-derivatives of an organic acid to an acceptor molecule selected from the group consisting of anthocyanins and anthocyanidins.

The acyltransferase can be any enzyme that is capable of catalysing transfer of one acyl residue from any of the acyl donors described herein below in the section "Acyl donor" to an anthocyanin and/or an anthocyanidin.

In one embodiment the acyltransferase is of the BAHD type. Thus, one or more acyltransferases, for example at least 50% of the acyltransferases, such as at least 75% of the acyltransferases, such as all acyltransferases to be used with the methods of the invention are BADH acyltransferases.

Nucleic acid molecules encoding BAHD acyltransferases can be identified by screening of gene transcripts present in anthocyanin-producing tissues of plants having a high level of anthocyanin production. Such plants for example include sweet potato, radish, carrot, Iris×hollandica, Oryza sativa, Solanum lycopersicon, Zea mays, Arabidopsis thaliana, Gentiana triflora, Lobelia erinus, Perilla frutescens, Ricinus communis, Medicago truncatula, Vitis vinifera, Phaseolus vulgaris, Salvia splendens or Petunia×hybrid. In particular the plants can be purple sweet potato (Ipomoea batata), black carrot (Daucus carota) and red radish (Raphanus sativus). The screening can use homology searching with known BAHD genes to identify additional nucleic acid molecules encoding BADH acyltransferases. For these enzymes certain protein motifs are conserved well enough to allow easy identification. The identified nucleic acid molecules can then be transferred to host cells or be used for in vitro production of acyltransferases to be used with the methods of the invention.

Exemplary GenBank Accession Numbers for BAHD acyltransferase nucleic acid molecules include, but are not limited to NM_126116.1, NM_113890.2, NM_124172.2, KF569647.1, JQ413189.1, XM_003622018.1, XM_003622017.1, XM_003616530.1, XM_003604576.1, XM_003600812.1, or XM_003591830.1.

This can for example be accomplished as described in Gang, D. R. (2005). Evolution of flavors and scents. Annu. Rev. Plant Biol. 56: 301-325. Thus, in one embodiment one or more acyltransferases to be used with the present invention may be a BAHD acyltransferase encoded by any of the BADH gene candidates described by Gang et al., 2005).

In another embodiment, the acyltransferase can belong to the EC 2.3.1-class of enzymes, including EC 2.3.1.18; EC 2.3.1.153; EC 2.3.1.171; EC 2.3.1.172; EC 2.3.1.173; EC 2.3.1.213; EC 2.3.1.214; EC 2.3.1.215; and similar enzymes.

In yet another embodiment, the acyltransferase can belong to the class of AHCT (anthocyanin o-hydroxy cinnamoyl transferase) enzymes. An exemplary GenBank Accession Number for an AHCT nucleic acid molecule includes, but is not limited to, AY395719.1.

According to the invention, enzymes of any of the above mentioned classes can be used individually or as mixtures.

Flavanones

As described herein above flavanones such as naringenin can be a precursor of several anthocyanidins. Thus, host cells of the invention can be capable of producing one or more flavanones (e.g., naringenin, butin, dihydrotricetin, eriodictyol, hesperetin, hesperidin, homoeriodictyol, isosakuranetin, naringin, pinocembrin, poncirin, sakuranetin, sakuranin, sterubin). In one example, naringenin can for example be prepared from an acyl donor, and in particular from p-coumaroyl-CoA.

Thus, the host cell can be capable of producing an acyl donor, and in particular p-coumaroyl-CoA. The biosynthesis pathway to various acyl donors is described herein below in the section "Acyl donor."

With reference to FIG. 1, synthesis of an acyl donor constitutes step 1. This section describes step 2, i.e. the biosynthesis of naringenin from an acyl donor, and in particular from p-coumaroyl-CoA.

The host cell can be capable of producing flavanones, e.g. naringenin. The host cell can naturally be capable of production of naringenin, but for example in embodiments of the invention where the host cell is a yeast or bacterial cell, then the host may not be able to naturally produce naringenin. In such embodiments the host cell can comprise heterologous enzyme nucleic acid molecules encoding all enzymes of the biosynthesis pathway to flavanones. For example, the host cell can comprise heterologous enzyme nucleic acid molecules encoding all the enzymes of the biosynthesis pathway for conversion of an acyl donor, such as p-coumaroyl-CoA to naringenin.

In particular, the host cell can comprise one or more of the following heterologous enzyme nucleic acid molecules, such as both of the following heterologous enzyme nucleic acid molecules:

i) a heterologous enzyme nucleic acid encoding a chalcone synthase ii) a heterologous enzyme nucleic acid encoding chalcone isomerase.

Exemplary GenBank Accession Numbers for chalcone synthase nucleic acid molecules include, but are not limited to, NM_121396.3, NM_001148774.1, NM_001280950.1, EF090604.2, NM_001281135.1, or AY044331.1.

Exemplary GenBank Accession Numbers for chalcone isomerase nucleic acid molecules include, but are not limited to, NM_001281104.1, NM_126020.2, NM_115370.3, Y00852.1, M91080.1, or AF233637.1.

Acyl Donor

The acyl donor can be any useful acyl donor. In particular, the acyl donor may be any moiety comprising an acyl residue, such as any donor moiety covalently coupled to an acyl residue. The acyl residue can in particular be the acyl part of an organic acid.

The donor moiety can, for example, be coenzyme A, and thus the acyl donor can, for example, be a coenzyme A-derivative of an organic acid. For example, the acyl donor may be a compound selected from the group consisting of acetyl-CoA, malonyl-CoA, coumaroyl-CoA, benzoyl-CoA, sinapoyl-CoA, feruloyl-CoA and caffeoyl-CoA. In particular, the acyl donor can be coumaroyl-CoA.

In embodiments of the invention relating to incubation mixtures, the acyl donor can be added directly to the incubation mixtures. However, in embodiments of the invention relating to use of host cells, the host cell can be capable of producing the acyl donor. Many host cells are capable of producing one or more acyl donors. For example, yeast cells are capable of producing malonyl-CoA.

Frequently, however, host cells are not capable of producing all desired acyl donors, in which case the host cells can comprise one or more heterologous enzyme nucleic acid molecules each encoding enzymes of the biosynthesis pathway of the specific acyl donor.

With reference to FIG. 1, the host cell can be capable of performing step 1 as shown in FIG. 1, and this section provides a description of how this step can be performed in a host cell, such as a yeast or bacterial cell.

Several biosynthesis pathways for conversion of glucose to an acyl donor are known. Where the host cell is a yeast or bacterial cell the cell can comprise a heterologous enzyme nucleic acid molecule encoding one or more enzymes of the biosynthesis pathway for conversion of glucose to an acyl donor, even though some of the required enzymatic activities typically are present in the host cell. Thus, frequently the acyl donor can be prepared using phenyl alanine or tyrosine as a substrate. Typically host cells, such as yeast or bacterial cells, are capable of producing phenyl alanine or tyrosine.

Thus, the host cell can comprise heterologous enzyme nucleic acid molecules encoding one or more enzymes of the biosynthesis pathway for conversion of phenyl alanine or tyrosine to feruloyl-CoA. For example the host cell can comprise heterologous enzyme nucleic acid molecules encoding all the enzymes of the biosynthesis pathway for conversion of phenyl alanine or tyrosine to feruloyl-CoA.

The host cell can also comprise heterologous enzyme nucleic acid molecules encoding one or more enzymes of the biosynthesis pathway for conversion of phenyl alanine or tyrosine to caffeoyl-CoA. For example the host cell can comprise heterologous enzyme nucleic acid molecules encoding all the enzymes of the biosynthesis pathway for conversion of phenyl alanine or tyrosine to caffeoyl-CoA.

The host cell can also comprise heterologous enzyme nucleic acid molecules encoding one or more enzymes of the biosynthesis pathway for conversion of phenyl alanine or tyrosine to sinapoyl-CoA. For example the host cell can comprise heterologous enzyme nucleic acid molecules encoding all the enzymes of the biosynthesis pathway for conversion of phenyl alanine or tyrosine to sinapoyl-CoA.

The host cell can also comprise heterologous enzyme nucleic acid molecules encoding one or more enzymes of the biosynthesis pathway for conversion of phenyl alanine or tyrosine to p-hydroxybenzoyl-CoA. For example the host cell can comprise heterologous enzyme nucleic acid molecules encoding all the enzymes of the biosynthesis pathway for conversion of phenyl alanine or tyrosine to p-hydroxybenzoyl-CoA.

In one embodiment the host cell can comprise heterologous enzyme nucleic acid molecules encoding one or more enzymes of the biosynthesis pathway for conversion of phenyl alanine or tyrosine to p-coumaroyl-CoA. For example the host cell can comprise heterologous enzyme nucleic acid molecules encoding all the enzymes of the biosynthesis pathway for conversion of phenyl alanine or tyrosine to p-coumaroyl-CoA.

In one embodiment the host cell can comprise heterologous enzyme nucleic acid molecules encoding one or more enzymes of the biosynthesis pathway for conversion of phenyl alanine to cinnamoyl-CoA. For example the host cell can comprise heterologous enzyme nucleic acid molecules encoding all the enzymes of the biosynthesis pathway for conversion of phenyl alanine to cinnamoyl-CoA.

In particular the host cell can comprise one or more of the following heterologous enzyme nucleic acid molecules, such as at least two of, such as least three of, for example at least four of, or all of the following heterologous enzyme nucleic acid molecules:

i) a heterologous enzyme nucleic acid encoding phenylalanine ammonia lyase (PAL); and
ii) a heterologous enzyme nucleic acid encoding tyrosine ammonia lyase (TAL); and
iii) a heterologous enzyme nucleic acid encoding cinnamate 4-monooxygenase; and
iv) a heterologous enzyme nucleic acid encoding 4-coumarate-CoA ligase Exemplary GenBank Accession Numbers for phenylalanine ammonia lyase (PAL) nucleic acid molecules include, but are not limited to AY303130.1, AY303129.1, NM_001111864.1, or AY303128.1.

An exemplary GenBank Accession Number for tyrosine ammonia lyase (TAL) nucleic acid molecules includes, but is not limited to KF765779.1.

Exemplary GenBank Accession Numbers for cinnamate 4-monooxygenase nucleic acid molecules include, but are not limited to, NM_128601.2, NM_001155686.1, FJ807780.1, or GU990522.1.

Exemplary GenBank Accession Numbers for 4-coumarate-CoA ligase nucleic acid molecules include, but are not limited to, AF106088.1, JX548316.1, JN120849.1, or AF106086.1.

Host Cell

The host cell to be used with the present invention may be any host cell. The host cell can readily be cultivated and also readily can be modified using recombinant techniques.

The host cell of the present invention can be any cell suitable for expression of heterologous nucleic acids. In one embodiment the host cell of the invention is a eukaryotic cell. In another embodiment the host cell is a prokaryotic cell.

In one embodiment, the host cell is a fungal cell such as a yeast or filamentous fungus. In particular the host cell may be a yeast cell.

In a further embodiment the yeast cell is selected from the group consisting of *Saccharomyces cerevisiae, Schizosaccharomyces pombe, Yarrowia lipolytica, Candida glabrata, Ashbya gossypii, Cyberlindnera jadinii,* and *Candida albicans*.

In general, yeasts and fungi are excellent host cells to be used with the present invention. They offer a desired ease of genetic manipulation and rapid growth to high cell densities on inexpensive media. For instance yeasts grow on a wide range of carbon sources and are not restricted to glucose. Thus, the host cells to be used with the present invention may be selected from the group of yeasts described below:

*Arxula adeninivorans* (*Blastobotrys adeninivorans*) is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Candida boidinii* is a methylotrophic yeast (it can grow on methanol). Like other methylotrophic species such as *Hansenula polymorpha* and *Pichia pastoris*, it provides an excellent platform for the production of heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. Details on how to download the software implemented in Python and experimental testing of predictions are known to those of skill in the art.

*Hansenula polymorpha* (*Pichia angusta*) is another methylotrophic yeast (see *Candida boidinii*). It can furthermore grow on a wide range of other substrates; it is thermotolerant and can assimilate nitrate (see also *Kluyveromyces lactis*). It has been applied to the production of hepatitis B vaccines, insulin and interferon alpha-2a for the treatment of hepatitis C, furthermore to a range of technical enzymes.

*Kluyveromyces lactis* is a yeast regularly applied to the production of kefir. It can grow on several sugars, most importantly on lactose which is present in milk and whey. It has successfully been applied among others to the production of chymosin (an enzyme that is usually present in the stomach of calves) for the production of cheese. Production takes place in fermenters on a 40,000 L scale.

*Pichia pastoris* is amethylotrophic yeast (see *Candida boidinii* and *Hansenula polymorpha*). It provides an efficient platform for the production of foreign proteins. Platform elements are available as a kit and it is worldwide used in academia for the production of proteins. Strains have been engineered that can produce complex human N-glycan (yeast glycans are similar but not identical to those found in humans).

*Saccharomyces cerevisiae* is the traditional baker's yeast known for its use in brewing and baking and for the production of alcohol. As protein factory it has successfully been applied to the production of technical enzymes and of pharmaceuticals like insulin and hepatitis B vaccines.

*Yarrowia lipolytica* is a dimorphic yeast (see *Arxula adeninivorans*) that can grow on a wide range of substrates. It has a high potential for industrial applications but there are no recombinant products commercially available yet.

In another embodiment the host cell is a microalgae such as *Chlorella* and *Prototheca*.

In another embodiment of the invention the host cell is a filamentous fungus, for example *Aspergillus*.

In further yet another embodiment the host cell is a plant cell. The host cell may be a cell of a higher plant, but the host cell may also be cells from organisms not belonging to higher plants for example cells from the moss *Physcomitrella patens*.

In another embodiment the host cell is a mammalian cell, such as a human, feline, porcine, simian, canine, murine, rat, mouse or rabbit cell.

The host cell may also be selected from the group consisting of CHO, CHO-K1, HEI193T, HEK293, COS, PC12, HiB5, RN33b, BHK cells.

As mentioned, the host cell can also be a prokaryotic cell such as a bacterial cell. If the cell is a prokaryotic cell the cell may be selected from, but not limited to *E. coli, Corynebacterium, Bacillus, Pseudomonas* and *Streptomyces* cells.

Depending on the particular host cell, the skilled person will be able to select conditions allowing growth of said cells.

Composition of Host Cells

The composition of host cells to be used with the methods of the invention can comprise a plurality of host cells comprising different combinations of heterologous nucleic acids selected from the group consisting of heterologous GT nucleic acids and heterologous AT nucleic acids.

A composition of the invention can comprise one or more host cells capable of producing one or more anthocyanins, wherein the host cells express at least one anthocyanidin, and wherein the host cells comprise one or more heterologous GT nucleic acid molecules and one or more heterologous AT nucleic acid molecules. The composition can comprise two or more host cells, wherein at least 2, 5, 10, 20, 50, 100, 500, 1,000, 10,000 or more of the host cells comprise different heterologous GT nucleic acid molecules or AT nucleic acid molecules. The cell can be microbial cell such as a yeast cell or a bacterial cell.

The composition of host cells can comprise at least 2, 5, 10, 20, 50, 100, 500, 1,000, 10,000, 100,000, 1,000,000, 10,000,000 or more host cells. In one embodiment of the invention the host cells in this composition all comprise different combinations of heterologous GT nucleic acid molecules and/or heterologous AT nucleic acid molecules.

The composition of host cells can comprise, for example at least 2, 5, 10, 100, 200, 300, 400, 500, 1,000, 10,000, 100,000 or more different heterologous GT nucleic acid molecules each encoding a different glycosyltransferase. The heterologous GT nucleic acid molecules can be comprised with different host cells, so that each host comprises in the range of 2 to 30, such as in the range of 2 to 20, for example in the range of 2 to 10, such as in the range of 2 to 5 different heterologous GT nucleic acid molecules each encoding a different glycosyltransferase.

The composition of host cells can comprise, for example, at least 2, 5, 10, 100, 200, 300, 400, 500, 1,000, 10,000, 100,000 or more different heterologous AT nucleic acid molecules each encoding a different acyltransferase. The heterologous AT nucleic acid molecules can be comprised with different host cells, so that each host comprises in the range of 2 to 30, such as in the range of 2 to 20, for example in the range of 2 to 10, such as in the range of 2 to 5 different heterologous AT nucleic acid molecules each encoding a different AT nucleic acid molecule.

Artificial Chromosomes

The host cells to be employed in the methods of the invention comprise one or more heterologous nucleic acids.

The heterologous nucleic acids can be expressed in the host by cloning them into expression cassettes, in which they are fused to regulatory nucleic acid molecules, allowing transcription and translation of the protein encoding sequence. Such cassettes can be maintained in the host by introducing them on self-replicating vectors, or by integrating them into the host genomes. Such approaches are known to those skilled in the art.

Alternatively, one or more of these heterologous nucleic acids can be comprised within an artificial chromosome. Thus, each host cell can comprise at least one artificial chromosome comprising heterologous GT nucleic acid molecules and/or heterologous AT nucleic acid molecules. In particular, each host cell can comprise at least one artificial chromosome comprising all the heterologous GT nucleic acid molecules and/or heterologous AT nucleic acid molecules comprised within said cell.

The heterologous nucleic acid molecules may be organized on said artificial chromosomes in expression cassettes. For example the heterologous nucleic acid molecules can be organized and processed as described in international applications WO02/059296, WO02/059297 and WO02/059290 (all of which are incorporated herein by reference), wherein the heterologous GT nucleic acid molecules and/or heterologous AT nucleic acid molecules can substitute the expressible nucleotide molecule described therein.

As used herein, the singular forms "a," "an", and "the" include plural referents unless the context clearly dictates otherwise. All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1: An Anthocyanidin Glycosylation Platform

Family 1 UDP-glucose dependent glucosyltransferases (UGTs) are used for the initial conversion of anthocyanidins into glycosylated anthocyanins. More than 300 Family 1 UGTs, including a large number which are flavonoid- and anthocyanidin-specific are used. The UGT enzymes are expressed in *E. coli* and purified on nickel columns (the enzymes are fused to a HIS tag). These purified enzymes constitute the Glycosylation element of the Anthocyanin Diversification Platform.

Establishing an Anthocyanidin Acylation Platform

About one hundred presently annotated anthocyanin acyltransferase genes or strong homologs thereof from Iris×hollandica, Oryza sativa, Solanum lycopersicon, Zea mays, Arabidopsis thaliana, Gentiana triflora, Lobelia erinus, Perilla frutescens, Ricinus communis, Medicago truncatula, Vitis vinifera, Phaseolus vulgaris, Salvia splendens or Petunia×hybrid are sourced by synthesis.

In addition transcriptomes of organisms containing particularly interesting acylated anthocyanins, i.e. purple sweet potato (Ipomoea batata), black carrot (Daucus carota) and red radish (Raphanus sativus) are prepared. The transcriptome analysis is made from the tissues producing and containing the anthocyanins in question. In these three transcriptomes we analyze for the presence of BAHD gene candidates by homology searching with the about 100 BAHD genes described above. The 20 most homologous expressed genes from each tissue are sourced by synthesis.

The combined 160 BAHD-like acyltransferase polynucleotides or homologs are inserted into E. coli expression vectors and transformed into E. coli. The polynucleotides are inserted in such a manner that they get in-frame fused to a histidine tag. After expression of each of the 160 BAHD acyltransferase clones the resulting expressed heterologous protein is purified using nickel columns. The purified proteins are kept as frozen glycerol stocks and constitute the Acylation element of the Anthocyanin Diversification Platform.

Making a Multitude of Anthocyanin Structures by Using an In Vitro Anthocyanin Diversification Platform An anthocyanidin substrate is mixed with pools of 10 different UGTs and 10 different acyltransferases, as well as 3 different sugar donors (e.g. UDP-glucose) and 3 different acyl donors (e.g. coumaroyl-CoA), in addition to a reaction buffer. After incubation at 30° C. for 3 hours reaction products are analysed using LC-MS. Reactions showing interesting products (i.e. with an MW indicating that the anthocyanidin substrate has been glycosylated as well as acylated) are "de-replicated" in the following way:

The same reaction is done again, but now split in 10, each having one of the 10 different UGTs present. The active UGT is identified using LC-MS. The experiment is repeated, now with this single UGT, the 10 acyltransferases, 3 acyl donors and each of the 3 sugar donors, in 3 different reactions. The active sugar donor is identified using LC-MS. The experiment is repeated, with the active UGT and the active sugar donor, 3 acyl donors, but in 10 reactions, each with one of the acyltransferases. The active acyltransferase is identified by LC-MS. The experiment is repeated, with the active UGT, the active sugar donor, the active acyltransferase, but in three reactions, each with one particular acyl donor. At the end of this a pathway for making a particular glycosylated and acylated anthocyanidin is identified.

Example 2: Establishment of Acyl Donor Biosynthesis in Yeast

Yeast already produces malonyl-CoA. We establish biosynthesis of p-coumaroyl-CoA in yeast in the following way: The enzymes phenylalanine ammonia lyase (PAL), cinnamate 4-monooxygenase and 4-coumarate-CoA ligase are all expressed in yeast, allowing conversion of yeast phenylalanine to coumaroyl-CoA. This is one example but similarly one could introduce biosynthesis in yeast of cinnamoyl-CoA, benzoyl-CoA, sinapoyl-CoA, feruloyl-CoA, caffeoyl-CoA or other acyl donors.

Establishment of Anthocyanidin Biosynthesis in Yeast

We establish biosynthesis of the anthocyanidin cyanidin in yeast in the following way: The enzymes chalcone synthase, chalcone isomerase, naringenin 3-dioxygenase, flavonoid 3'-monooxygenase, bifunctional dihydroflavonol 4-reductase/flavanone 4-reductase and leucoanthocyanidin dioxygenase are all expressed in the p-coumaroyl-CoA biosynthesizing yeast described above, allowing production of cyanidin. This is one example, but similarly one could introduce biosynthesis in yeast of delphinidin, petunidin, rosinidin, malvidin, pelargonidin or other anthocyanidins.

Making a Multitude of Anthocyanin Structures by Using an In Vivo Anthocyanin Diversification Platform We make eYACs (expression yeast artificial chromosomes) consisting of genes picked at random from the collection of 300 glycosyltransferases (UGTs) and 160 BAHD-type acyltransferases prepared as described in Example 1. These are inserted in so-called gene expression cassettes from which expression in yeast can be controlled. Random eYACs containing ca. 50 of such expression cassettes are made and transformed into yeast strains as described above having the ability to form both acyl donors (e.g. p-coumaroyl-CoA) and anthocyanidins (e.g. cyanidin). The resulting library is large, consisting of several thousands of independent clones, each containing a different eYAC, expressing different combinations of UGTs and acyltransferases. We pick 10,000 random eYAC containing clones, grow these under conditions where acyl donor and anthocyanidin is being formed and where expression from the gene cassettes residing on the eYACs takes place. We then subject the small molecular content of the resulting yeast cultures to LC-MS analysis, in order to identify resulting known or unknown glycosylated and acylated anthocyanidins. In this way a large and diverse array of anthocyanidins are identified.

We claim:

1. A method of identifying modified anthocyanins with improved stability, color, or hue using a screening method comprising the steps of:
    (a) providing one or more microbial host cells capable of producing at least one anthocyanidin, wherein said host cells comprise one or more heterologous glycosyltransferase (GT) nucleic acid molecules and one or more heterologous acyltransferase (AT) nucleic acid molecules;
    (b) cultivating said host cells under conditions allowing growth of said cells and production of at least one anthocyanin thereby;
    (c) screening said host cells and/or culture medium for modified anthocyanins with improved stability, color, or hue; and
    (d) identifying modified anthocyanins with improved stability, color, or hue.

2. A method of identifying modified anthocyanins with improved stability, color, or hue using a screening method comprising the steps of:
    (a) providing one or more microbial host cells capable of producing at least one anthocyanidin, wherein said host cells comprise one or more heterologous glycosyltransferase (GT) nucleic acid molecules, one or more heterologous acyltransferase (AT) nucleic acid molecules, or both one or more heterologous GT nucleic acid molecules and one or more heterologous AT nucleic acid molecules;

(b) cultivating said host cells under conditions allowing growth of said cells and production of at least one anthocyanin thereby;
(c) screening said host cells and/or culture medium for modified anthocyanins with improved stability, color, or hue; wherein the screening comprises:
  (i) isolating one or more anthocyanins from said host cells and/or from culture medium of the host cells;
  (ii) exposing the one or more anthocyanins to steadily increasing concentrations of a reagent to effect a change in the color intensity of the one or more anthocyanins;
  (iii) comparing the concentration where a loss of color intensity occurs with a control, wherein the ability to retain color intensity at higher concentrations of exposure to the reagent than the control indicates improved anthocyanin stability
and
(d) identifying modified anthocyanins with improved stability, color, or hue.

3. The method according to claim 2, wherein the reagent is a base, light, heat, and/or oxygen.

4. The method according to claim 2, wherein the reagent is a base.

5. The method according to claim 2, wherein the reagent comprises lithium hydroxide, sodium hydroxide, potassium hydroxide, and rubidium hydroxide.

6. The method according to claim 5, wherein the reagent further comprises sodium hydroxide.

7. A method of identifying a host cell capable of producing a modified anthocyanin with a predetermined property, said method comprising the steps of:
(a) providing a composition of microbial host cells, wherein each host cell is capable of producing at least one anthocyanidin, and wherein each host cell comprises one or more heterologous glycosyltransferase (GT) nucleic acid molecules and one or more heterologous acyltransferase (AT) AT nucleic acid molecules;
(b) cultivating said host cells under conditions allowing growth of said host cells and production of at least one anthocyanin thereby;
(c) screening the composition of host cells, for host cells producing a modified anthocyanin with the predetermined property; and
(d) selecting said host cell;
wherein a host cell capable of producing a modified anthocyanin with a predetermined property is identified.

8. A method of producing modified anthocyanins with improved stability, color, or hue, said method comprising the steps of:
(a) providing two or more microbial host cells capable of producing at least one anthocyanidin, wherein each host cell comprises one or more heterologous GT nucleic acid molecules and one or more heterologous AT nucleic acid molecules;
(b) cultivating said host cells under conditions allowing growth of said cells and production of modified anthocyanins thereby; and
(c) isolating one or more modified anthocyanins from the host cells and/or from the culture medium.

9. The method of claim 1, wherein said one or more host cells are capable of producing an anthocyanidin of the formula I

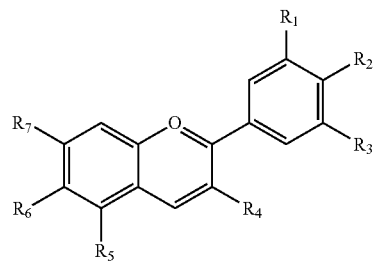

wherein
$R_1$ is selected from the group consisting of H, —OH and $OCH_3$; and
$R_2$ is selected from the group consisting of —H and —OH; and
$R_3$ is selected from the group consisting of —H, —OH and —$OCH_3$; and
$R_4$ is selected from the group consisting of —H and —OH; and
$R_5$ is selected from the group consisting of —OH and —$OCH_3$; and
$R_6$ is selected from the group consisting of —H and —OH; and
$R_7$ is selected from the group consisting of —OH and —$OCH_3$.

10. The method of claim 1, wherein the anthocyanidin is selected from the group consisting of aurantinidin, cyanidin, delphinidin, europinidin, luteolinidin, pelargonidin, malvidin, peonidin, petunidin and rosinidin.

11. The method of claim 1, wherein the one or more host cells comprise one or more heterologous enzyme nucleic acid molecules, and wherein each heterologous enzyme nucleic acid molecule encodes an enzyme of the aurantinidin, cyanidin, delphinidin, europinidin, luteolinidin, pelargonidin, malvidin, peonidin, petunidin or rosinidin biosynthesis pathway.

12. The method according to claim 11, wherein the host cells comprise one or more heterologous enzyme nucleic acid molecules each encoding an enzyme of the cyanidin biosynthesis pathway.

13. The method according to claim 12, wherein the host cell comprises one or more of the following heterologous enzyme nucleic acid molecules encoding the polynucleotides comprising CHS, CHI, F3H, F3'H, F3'5'H, DFR, ANS (LDOX), FLS, LAR, and ANR.

14. The method of claim 1, wherein the one or more host cells are capable of producing one or more flavanones.

15. The method according to claim 14, wherein the one or more host cells comprise one or more heterologous enzyme nucleic acid molecules each encoding an enzyme of the naringenin biosynthesis pathway.

16. The method according to claim 14, wherein the one or more host cells comprise one or more of the following heterologous enzyme nucleic acid molecules:
(a) a heterologous enzyme nucleic acid molecule encoding naringenin-chalcone synthase; or
(b) a heterologous enzyme nucleic acid molecule encoding chalcone isomerase.

17. The method according to claim 14, wherein the one or more host cells comprise one or more heterologous enzyme nucleic acid molecules each encoding an enzyme of the coumaoryl-CoA biosynthesis pathway.

18. The method according to claim 1, wherein the one or more host cells comprise one or more of the following heterologous enzyme nucleic acid molecules:
- (a) a heterologous enzyme nucleic acid encoding phenylalanine ammonia lyase (PAL);
- (b) a heterologous enzyme nucleic acid encoding cinnamate 4-monooxygenase; or
- (c) a heterologous enzyme nucleic acid encoding 4-coumarate-CoA ligase.

19. The method according to claim 1, wherein at least 10 or more host cells each comprise different combinations of heterologous GT nucleic acid molecules and/or heterologous AT nucleic acid molecules.

20. The method according to claim 1, wherein at least 10 host cells comprise at least 10 different heterologous GT nucleic acid molecules each encoding a different glycosyltransferase.

* * * * *